US 10,548,509 B2

(12) United States Patent
Rettedal et al.

(10) Patent No.: US 10,548,509 B2
(45) Date of Patent: Feb. 4, 2020

(54) ANIMAL MONITORING SYSTEM

(71) Applicant: ST Reproductive Technologies, LLC, Navasota, TX (US)

(72) Inventors: Nicholas P. Rettedal, Loveland, CO (US); Stephen M. Weilnau, Greeley, CO (US); Scott R. Cockroft, Greeley, CO (US); Billy J. Yeager, Gilbert, AZ (US); Jerry A. Hornick, Gold Canyon, AZ (US); John B. Lienau, Milwaukee, WI (US)

(73) Assignee: ST Reproductive Technologies, LLC, Navasota, TX (US)

( * ) Notice: Subject to any disclaimer, the term of this patent is extended or adjusted under 35 U.S.C. 154(b) by 602 days.

(21) Appl. No.: 13/824,270

(22) Filed: Mar. 15, 2013

(65) Prior Publication Data

US 2013/0197323 A1    Aug. 1, 2013

Related U.S. Application Data

(63) Continuation-in-part of application No. PCT/US2011/001788, filed on Oct. 19, 2011.
(Continued)

(51) Int. Cl.
*A61B 5/07* (2006.01)
*A01K 11/00* (2006.01)
*A61D 7/00* (2006.01)

(52) U.S. Cl.
CPC ............ *A61B 5/073* (2013.01); *A01K 11/007* (2013.01); *A61D 7/00* (2013.01)

(58) Field of Classification Search
CPC . A01K 11/007; A61B 5/073; G06K 19/07749
See application file for complete search history.

(56) References Cited

U.S. PATENT DOCUMENTS

| 5,482,008 | A |   | 1/1996 | Stafford et al. |
| 5,532,692 | A | * | 7/1996 | Tatsuya ........................ 340/10.1 |

(Continued)

FOREIGN PATENT DOCUMENTS

| EP | 2314154 A1 |   | 4/2011 |
| JP | 2007089892 A | * | 4/2007 |

(Continued)

OTHER PUBLICATIONS

International Patent Cooperation Treaty Patent Application No. PCT/US2011/001788, filed Oct. 19, 2011.
(Continued)

*Primary Examiner* — Christian Jang
*Assistant Examiner* — Michael Catina
(74) *Attorney, Agent, or Firm* — Ryan Christensen; Hashim Rahman

(57) ABSTRACT

An animal monitoring device configured as a bolus for oral administration to reside in an animal's stomach. The bolus has a substantially inert solid body with a hollow inside space to receive the animal monitoring device. The animal monitoring device includes a radio frequency generator, an animal identification information encoder for outputting the animal identification information of the particular animal. The animal monitoring device can further include sensors to detect physiological and non-physiological animal characteristics such as temperature and a sensed animal characteristic encoder for outputting sensed animal characteristic information. The animal monitoring device intermittently transmits encoded animal identification information and sensed animal characteristic information to a receiver which transmits the encoded information as packets to a specialized computer which allows a computer user access to decoded animal identification information and sensed animal characteristic information as numeric values.

14 Claims, 7 Drawing Sheets

Related U.S. Application Data

(60) Provisional application No. 61/455,419, filed on Oct. 19, 2010.

(56) References Cited

U.S. PATENT DOCUMENTS

| | | | |
|---|---|---|---|
| 5,697,384 A * | 12/1997 | Miyawaki | A01K 11/007 128/899 |
| 5,818,354 A | 10/1998 | Gentry | |
| 5,963,132 A | 10/1999 | Yoakum | |
| 5,984,875 A * | 11/1999 | Brune | 600/549 |
| 6,059,733 A | 5/2000 | Brune et al. | |
| 6,085,751 A | 7/2000 | Taparia | |
| 6,099,482 A | 8/2000 | Brune et al. | |
| 6,371,927 B1 | 4/2002 | Brune et al. | |
| 6,416,782 B1 | 7/2002 | Maas | |
| 6,702,185 B1 * | 3/2004 | Zercher | 235/488 |
| 7,441,515 B2 | 10/2008 | Renz et al. | |
| 7,962,096 B2 | 6/2011 | Cox | |
| 8,001,168 B2 | 8/2011 | Tsuyuzaki | |
| 8,545,436 B2 | 10/2013 | Robertson et al. | |
| 8,547,248 B2 | 10/2013 | Zdeblich et al. | |
| 8,588,887 B2 | 11/2013 | Arneson et al. | |
| 8,640,712 B2 | 2/2014 | Ardrey, Jr. | |
| 8,694,091 B2 | 4/2014 | Birk et al. | |
| 8,771,201 B2 | 7/2014 | Gabriel et al. | |
| 2001/0001176 A1 | 5/2001 | Caja Lopez et al. | |
| 2002/0128542 A1 | 9/2002 | Van Over | |
| 2004/0133131 A1 | 7/2004 | Kuhn et al. | |
| 2004/0155782 A1 * | 8/2004 | Letkomiller et al. | 340/573.3 |
| 2005/0134452 A1 | 6/2005 | Smith | |
| 2005/0145187 A1 | 7/2005 | Gray | |
| 2007/0003612 A1 * | 1/2007 | Williams | A61B 5/07 424/451 |
| 2007/0136154 A1 | 6/2007 | Chung | |
| 2007/0156016 A1 * | 7/2007 | Betesh et al. | 600/102 |
| 2008/0104209 A1 | 5/2008 | Singhal et al. | |
| 2008/0236500 A1 | 10/2008 | Hodges et al. | |
| 2008/0314325 A1 | 12/2008 | Hempstead et al. | |
| 2009/0030279 A1 | 1/2009 | Zander et al. | |
| 2009/0182207 A1 | 7/2009 | Riskey et al. | |
| 2009/0187392 A1 * | 7/2009 | Riskey et al. | 703/11 |
| 2010/0030025 A1 * | 2/2010 | Segawa et al. | 600/118 |
| 2010/0302039 A1 | 12/2010 | Goto et al. | |
| 2011/0212782 A1 | 9/2011 | Thompson et al. | |
| 2011/0301437 A1 | 12/2011 | Gabriel et al. | |
| 2012/0068848 A1 | 3/2012 | Campbell et al. | |
| 2013/0197323 A1 | 8/2013 | Rettedal et al. | |
| 2013/0231188 A1 | 9/2013 | Berberich et al. | |
| 2014/0240088 A1 | 8/2014 | Robinette et al. | |
| 2014/0368338 A1 | 12/2014 | Rettedal et al. | |
| 2016/0360994 A1 | 12/2016 | Rettedal et al. | |

FOREIGN PATENT DOCUMENTS

| | | |
|---|---|---|
| WO | 2011/079338 A2 | 7/2011 |
| WO | 2012/173502 A1 | 12/2012 |
| WO | 2016/201242 | 12/2016 |

OTHER PUBLICATIONS

U.S. Appl. No. 61/455,419, filed Oct. 19, 2010.
U.S. Appl. No. 13/391,614, filed Feb. 21, 2012.
International Patent Corporation Treaty Patent Application No. PCT/US2010/002509, filed Sep. 14, 2010.
U.S. Appl. No. 61/276,723, filed Sep. 15, 2009.
Boehmer, et al. Effects of Temperature of Consumed Water on Rumen Temperature of Beef Cows. Oklahoma Agricultural Experiment Station, Dec. 2009, 4 total pages.
Cooper-Prado, et al. Relationship of Ruminal Temperature with Parturition and Estrus of Beef Cows. J Anim Sci, Apr. 2011, 89:1020-1027; published ahead of print Dec. 17, 2011.
Smartstock USA. Website, http://www.smartstock-usa.com, originally downloaded Dec. 30, 2011, 12 total pages.
Nikitin et al. Theory and Measurement of Backscattering from RFID Tags; IEEE Antennas and Propagation Magazine, Dec. 2006, 48(6):212-218.
Hach. Digital Inductive Conductivity Sensor, Convertible Body Style. Website, http:/www.hach.com, product page downloaded Mar. 5, 2014, 2 total pages.
Caja et al. Development of a ceramic bolus for the permanent electronic identification of sheep, goat and cattle. Computers and Electronics in Agriculture (1999), vol. 24, pp. 45-63.
Fallon et al. Electronic Animal Identification. Grange Research Center, Beef Production Series No. 46, pp. 1-54.
Ghirardi et al. Evaluation of the retention of electronic identification boluses in the forestomachs of cattle. Journal of Animal Science (2006), vol. 84, pp. 2260-2268.
Ghirardi et al. Retention of different sizes of electronic identification boluses in the forestomachs of sheep. Journal of Animal Science (2006), vol. 84, pp. 2865-2872.
Scanga et al. Development of computational models for the purpose of conducting individual livestock and premises traceback investigations utilizing National Animal Identification System-compliant data. Journal of Animal Science (2007), vol. 85, pp. 503-511.
European Patent Application No. 11834759.0; Office Action dated May 24, 2016, 8 pages total.
Corresponding NZ Patent Application No. 610343; OA dated May 12, 2013, 3 total pages.
Corresponding AU Patent Application No. 2010296053; Patent Examination Report No. 1, dated Jul. 16, 2014, 3 total pages.
International PCT Patent Application No. PCT/US2016/066012; International Search Report and Written Opinion dated Mar. 3, 2017, 9 pages total.
U.S. Appl. No. 14/970,289, filed Dec. 15, 2015.
Corresponding Australian Patent Application No. 2016213866; Office Action dated Mar. 10, 2017; 3 pages.
Carné et al. Modeling the retention of rumen boluses for the electronic identification of goats. J Dairy Sci, Feb. 2011, 94(2), pp. 716-726 (abstract only, 2 pages total).
New Zealand patent application No. 599357; OA dated Oct. 19, 2012, 1 page.
New Zealand patent application No. 599357; OA dated Feb. 8, 2013, 1 page.
New Zealand patent application No. 599357; Letters Patent dated Sep. 3, 2012, 1 page.
Corresponding New Zealand patent application No. 610343; OA dated Nov. 11, 2013, 3 total pages.
International Search Report and Written Opinion of the International Search Authority dated May 21, 2012 issued in related PCT application No. PCT/US2011/001788.
Australian Examination Report dated Jul. 1, 2019 is related AU application No. 2018204527.

\* cited by examiner

ANIMAL MONITORING SYSTEM

This application is a continuation-in-part of International Patent Cooperation Treaty Application No. PCT/US2011/001788, filed Oct. 19, 2011, which claims the benefit of U.S. Provisional Patent Application No. 61/455,419, filed Oct. 19, 2010, each hereby incorporated by reference herein.

I. TECHNICAL FIELD

Generally, an animal monitoring device configured as a bolus for oral administration to reside in an animal's stomach. The bolus has a substantially inert solid body which contains within an animal monitoring device. The animal monitoring device includes a radio frequency generator, an animal identification information encoder for outputting animal identification information of the particular animal. The animal monitoring device can further include sensors to detect one or more physiological and non-physiological sensed animal characteristics and a sensed animal characteristic encoder for outputting sensed animal characteristic information. The animal monitoring device further includes a first radio frequency generator which transmits encoded animal identification information and sensed animal characteristic information in a first radio frequency signal to a radio frequency reader which assembles and transmits encoded information as data packets to a specialized computer which allows a computer user access to decoded animal identification information and decoded sensed animal characteristic information as numeric values. The animal monitoring device can further include a radio frequency signal receiver capable of receiving a second radio frequency signal generated by a second radio frequency generator having a location outside of the animal and a microcontroller having a programmable module operable to control the radio frequency signal generator, the sensors, the animal identification information encoder, the sensed animal characteristic encoder, and the radio frequency signal receiver. The specialized computer or the reader can be further configured to generate the second radio frequency signal processed by the microcontroller to reprogram the programmable module to correspondingly alter operation of the radio frequency signal generator, one or more of the sensors, the animal identification information encoder, the sensed animal characteristic encoder, and the radio frequency signal receiver.

II. BACKGROUND

A variety of animal monitoring devices may be used to remotely track animal location and remotely sense the temperature of animals. Certain of these devices include an orally administered, inserted, or ingested bolus containing microprocessors for processing animal identification information and the signal from a temperature sensor to provide encoded data representations which can be transmitted by radio-frequency to a radio-frequency receiver. However, certain problems remain unresolved which relate to the structure and function of the bolus electrical circuitry and the transmission of encoded data representations by these conventional animal monitoring devices.

One problem related to conventional bolus may be that there is no magnet located within the bolus which generates a magnetic field to collect metal materials ingested by the animal such as wire, nails, screws, tacks, barbed wire, or the like. Alternately, conventional bolus may contain a magnet, but the magnetic field generated may dispose attracted metal elements in an orientation which projects outwardly from the bolus. These projecting metal elements can cause injury to the animal.

Another problem related to conventional bolus can be that the magnet has a location sufficiently close to or as a part of the components generating the radio-frequency which carries encoded data representations generated by the microcontroller or processor elements resulting in loss of encoded data representations during transmission to the radio frequency receiver.

Another problem related to conventional bolus may be that the mass of the animal in which the bolus has a location can demodulate the frequency of the radio signal such that the radio signal has a different frequency at the point of transmission than the frequency of the radio signal after passing through the mass of the animal. Accordingly, encoded data representations can be intermittently interrupted or portions or all of the transmitted encoded data representations can be lost.

As to each of these substantial problems, the animal monitoring system described herein provides a solution.

III. DISCLOSURE OF INVENTION

Accordingly, a broad object of embodiments of the invention can be to provide a bolus orally administrable for retention in the digestive tract of an animal which contains an animal monitoring device having a structure and a function which improves transmission of encoded animal identification information and encoded sensed animal characteristic information from within an animal to a radiofrequency reader.

Another broad object of embodiments of the invention can be to provide a bolus which includes one or more magnets disposed to generate one or more magnetic fields having a configuration which attracts metal objects to the external surface of the body of the bolus but avoids disposing such metal objects in outwardly projecting relation the external surface of the body of the bolus.

Another broad object of embodiments of the invention can be to provide an animal monitoring device on a printed circuit board which can be sufficiently isolated from the one or more magnets to allow transmission of encoded animal identification information and sensed animal characteristic information without interruption or loss of encoded information.

Another broad object of the invention of the invention can be to provide a network frequency match element which functions as part of the animal monitoring device to compensate for the mass of the animal such that the radiofrequency signal generated by the animal monitoring device antenna located inside the animal can be received by the radio frequency reader antenna located outside of the animal.

Naturally further objects of the invention are disclosed throughout the detailed description of the preferred embodiments of the invention and the figures.

IV. BRIEF DESCRIPTION OF THE DRAWINGS

Figure 9:
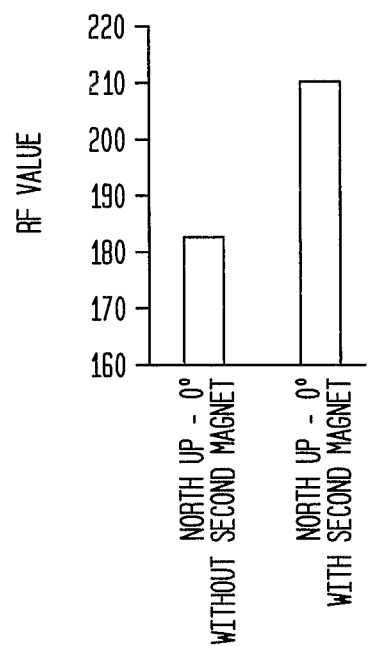

FIG. 9 is a bar graph which compares strength of radio frequency transmission with the first magnet contained in the bolus oriented to provide greatest strength of radio frequency transmission as compared to strength of radio frequency transmission with the first magnet contained in the bolus oriented to provide greatest strength of radio frequency transmission with a second magnet outside of the bolus magnetically coupled to the first magnet.

V. MODE(S) FOR CARRYING OUT THE INVENTION

Figure 1:
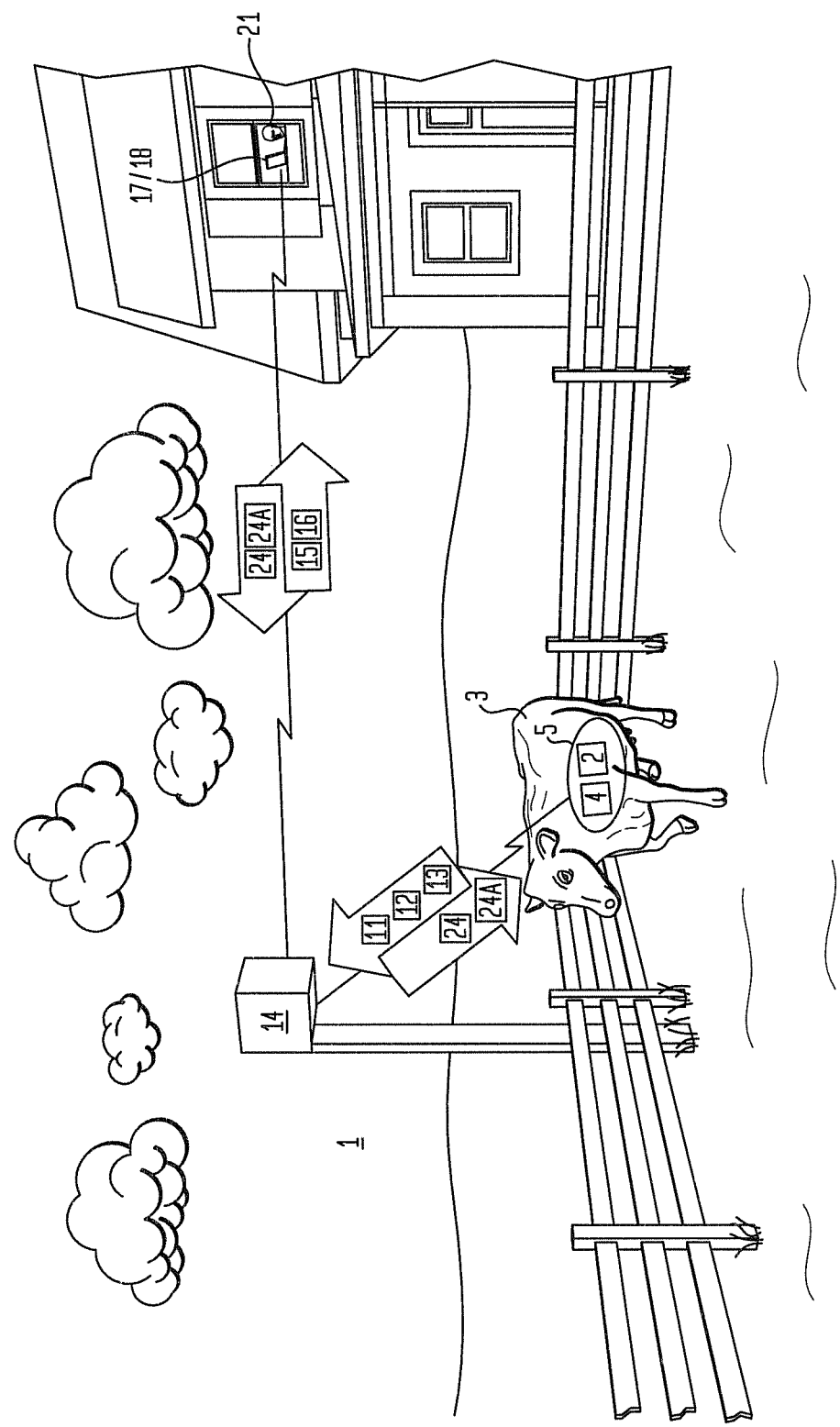
FIG. 1 is diagram which shows a particular method of using an embodiment of the animal monitoring system.
Figure 2:
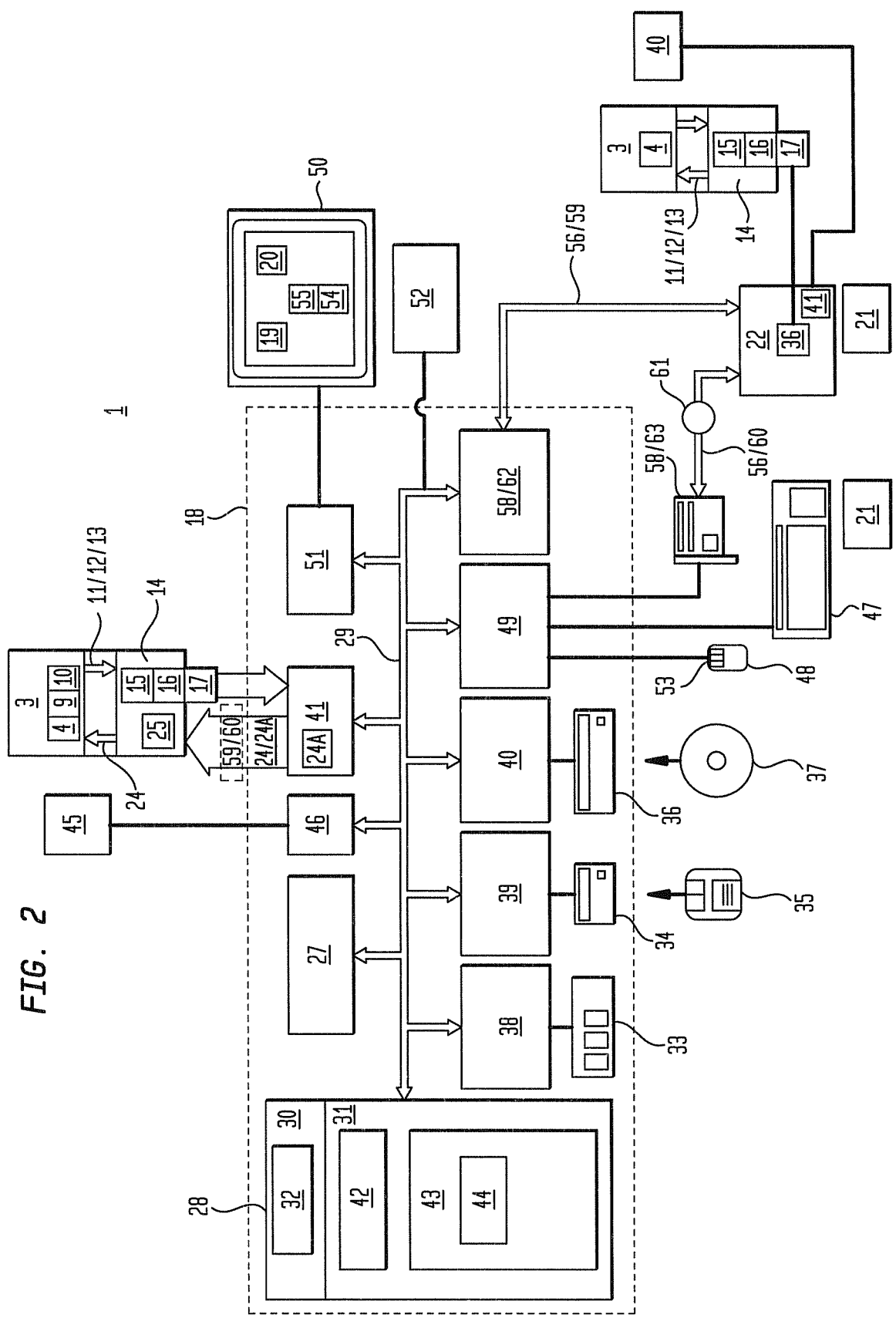
FIG. 2 is a block diagram which shows a particular embodiment of a specialized computer in relation to a particular embodiment of a radio frequency reader and bolus.

Now referring primarily to FIGS. 1 and 2, which illustrate a general computer implemented method of using an animal monitoring system (1) to monitor one or more sensed physiological and non-physiological parameters of an animal (3) (also referred to as "sensed animal characteristics (2)"). A bolus (4) can be orally administered to reside in a reticulum (5) of the animal (3), including ruminant animals such as cows, deer sheep, or the like although particular embodiments of the bolus (4) can be attached to or implanted in an animal (3) whether or not ruminant animals, to reside at other locations.

Figure 4:
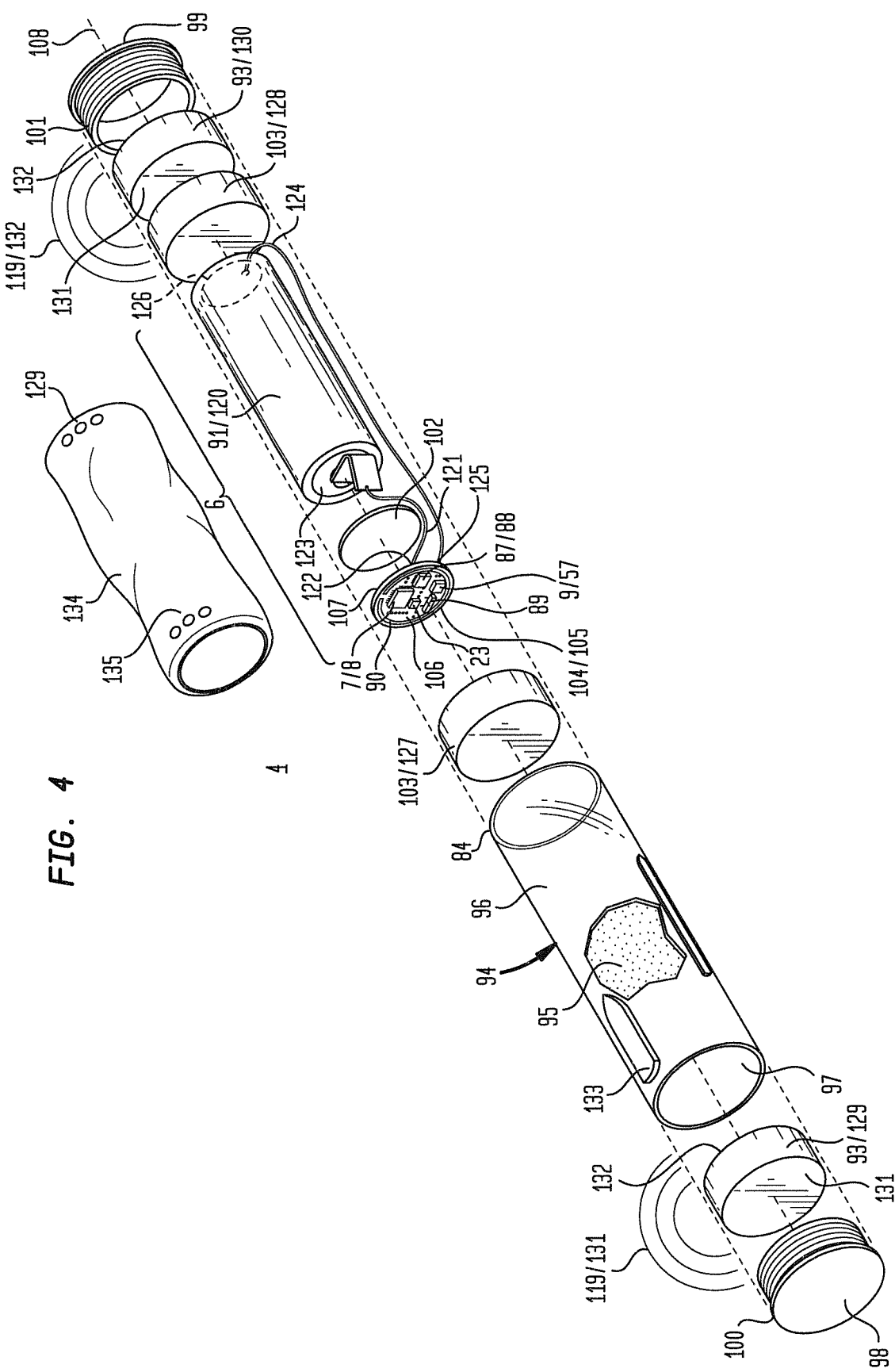
FIG. 4 is an exploded view of a particular embodiment of the bolus.
Figure 5:
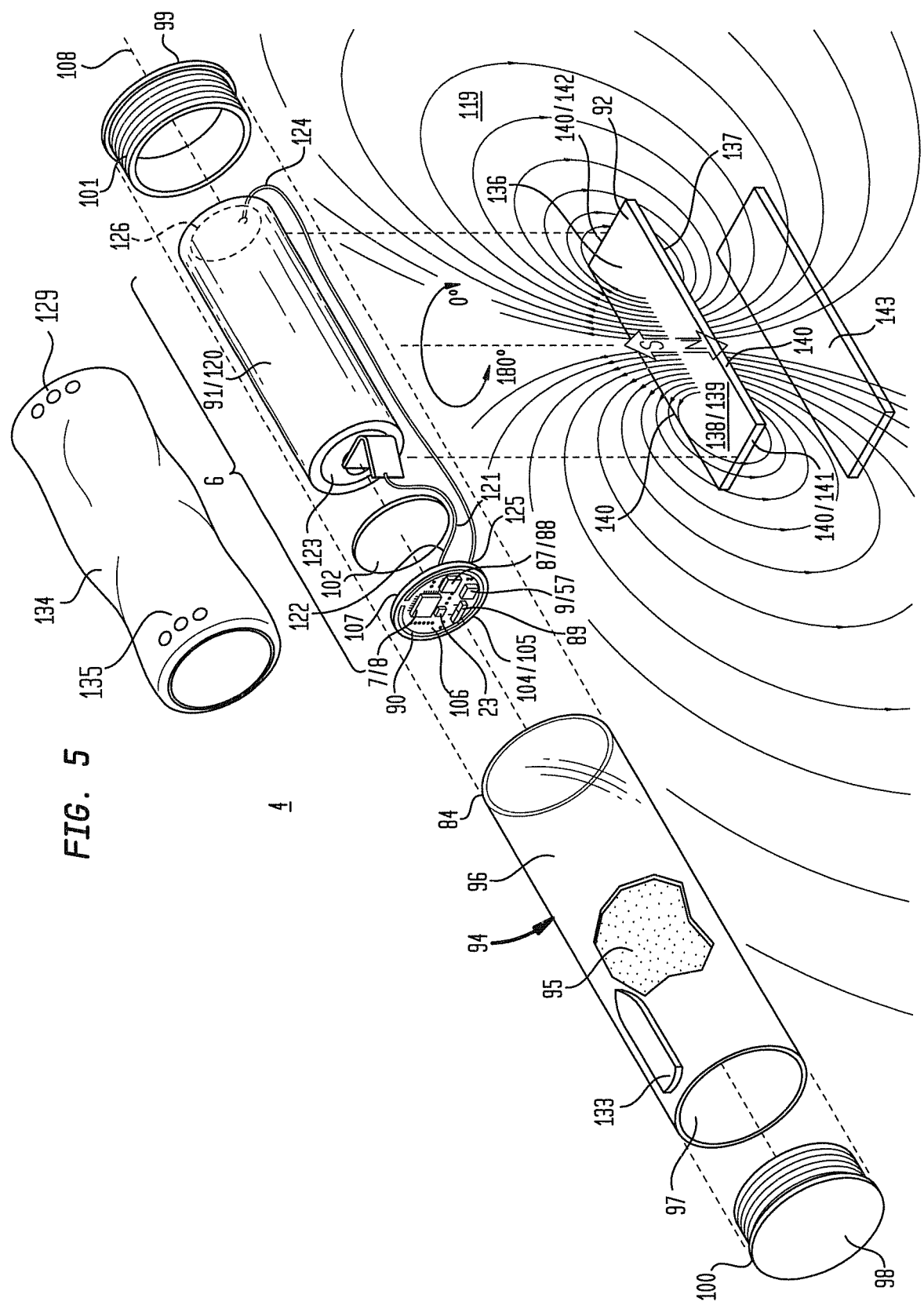
FIG. 5 is an exploded view of another particular embodiment of the bolus.
Figure 6:
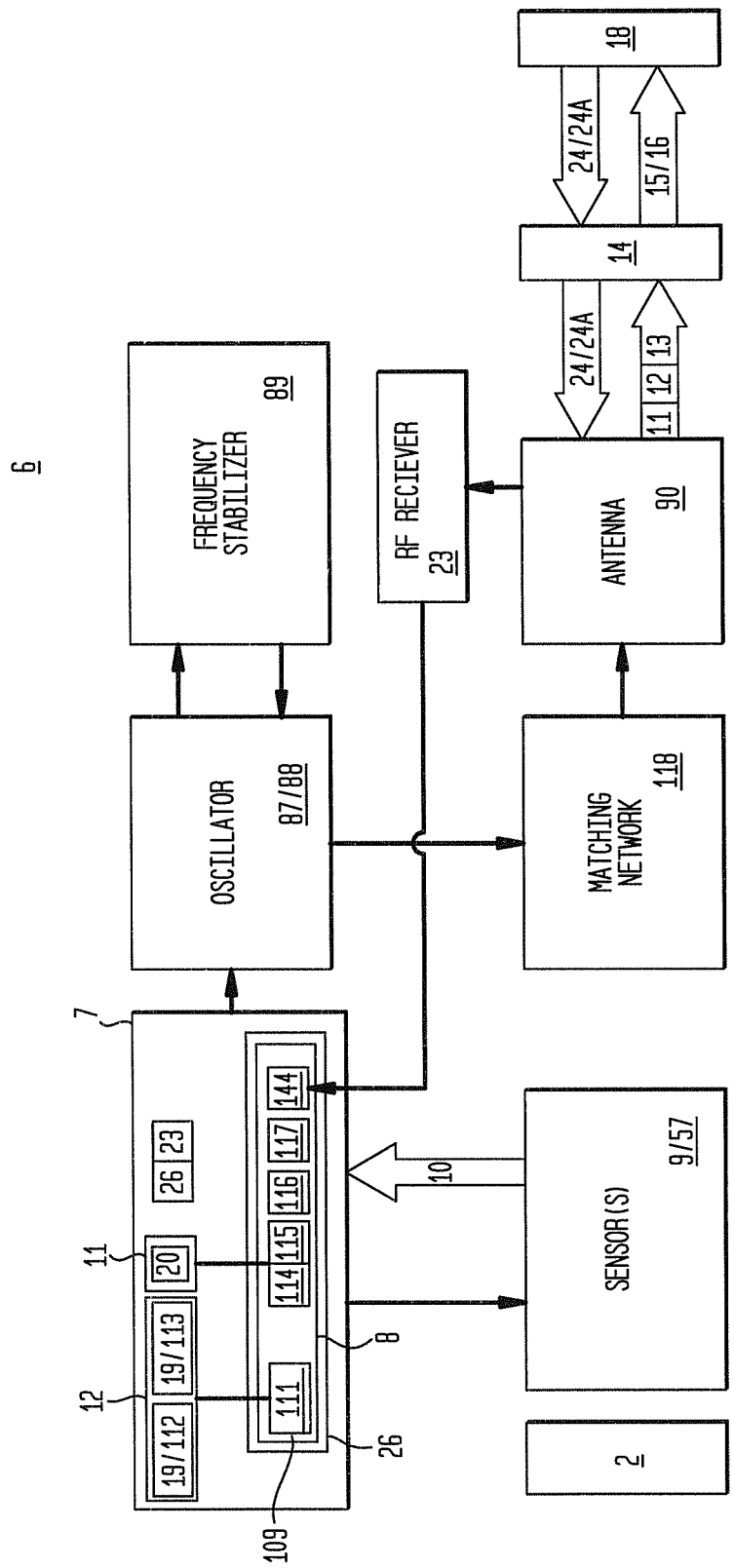
FIG. 6 is block diagram of a particular embodiment of the animal monitoring device which can be contained in a various embodiments of the bolus.

The bolus (4) can include an animal monitoring device (6)(as shown in the examples of FIGS. 4 and 5) including one more sensors (9). Each of the one or more sensors (9) can generate a sensor signal (10)(as shown in the example of FIG. 6) which varies based on change in the sensed animal characteristic (2). A microcontroller (7) having one or more processors (8) which operate to continuously or intermittently transform the analog or digital sensor signal (10) from the one or more sensors (9) to generate encoded sensed animal characteristic information (11). The encoded sensed characteristic information (11) varies based on change in the sensor signal (10) corresponding to change in the sensed animal characteristic (2). The animal monitoring device (6) can further generate encoded animal identification information (12) unique to each individual monitored animal (3). The animal monitoring device (6) can further operate to generate and transmit a first radio frequency signal (13) (also referred to as a "first RF signal") which can carry encoded animal identification information (12) and encoded sensed animal characteristic information (11).

Again referring primarily to FIGS. 1 and 2, one or more radio frequency reader(s)(14) can be located to receive the first radiofrequency signal (13) carrying the encoded animal identification information (12) and the encoded sensed animal characteristic information (11). As to particular embodiments, the one or more radiofrequency readers (14) can further operate to decode the received first radiofrequency signal (13) and generate one or more bit segments (15) representing the encoded animal identification information (12) and representing the encoded sensed animal characteristic information (11)(as shown in the example FIG. 3). As to particular embodiments, the one or more radio frequency readers (14) can further operate to assemble the bit segments (15) into a data packet (16) which can be transmitted and received by a wired or wireless reception device (17). The reception device (17) can transfer the data packet (16) to a specialized computer (18) for transforming the bit segments (15) to output an animal identification value (19) and to output a sensed animal characteristic value (20). A computer user (21) can access the sensed animal characteristic value (20) associated with the animal identification value (19) (along with other information encoded by the animal monitoring device (6) or the radio frequency reader (14) or a remote second computer (22)) by use of a specialized computer (18).

Figure 3:
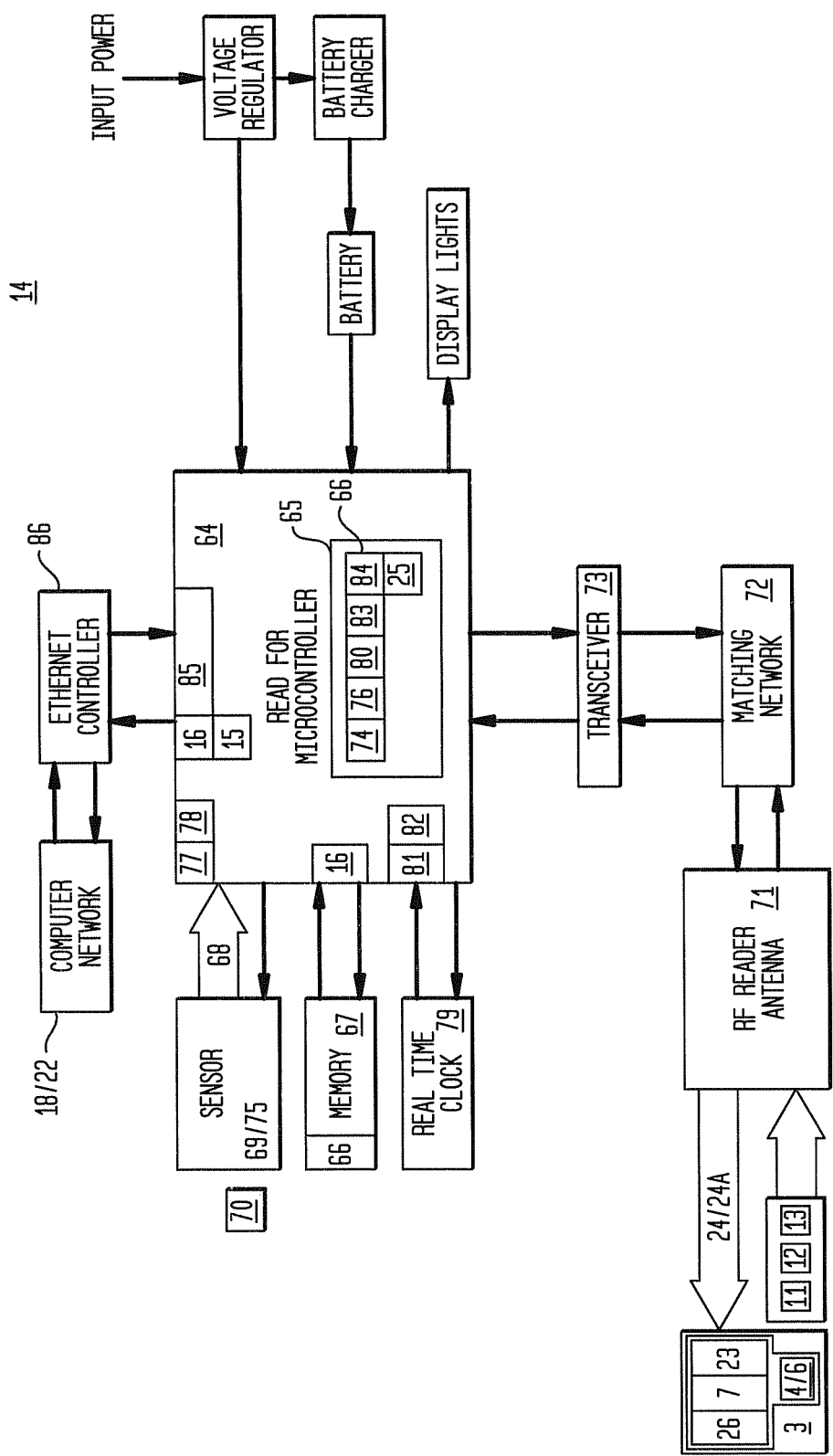
FIG. 3 is a block diagram which shows a particular embodiment of a radio frequency reader.

As to particular embodiments of the animal monitoring system (1) the animal monitoring device (6) can further include a radio frequency signal receiver (23) capable of receiving a second radio frequency signal (24) carrying programming data (24A) generated by a second radio frequency generator (25) having a location outside of the monitored animal (3). The second radio frequency signal (24) carrying programming data (24A) can be processed by the microcontroller (7) to reprogram a programmable module (26) to correspondingly alter the operation of the animal monitoring device (6), regardless as to whether the bolus (4) containing the animal monitoring device (6) has a location outside of the animal (3) or has a location inside of the animal (3). To facilitate reprogramming the programmable module (26) the specialized computer (18) or the radio frequency reader(s)(14) can be configured to generate the second radiofrequency signal (24) based on computer user (21) interaction; although as to particular embodiments the specialized computer (18) can be configured to send programming data (24A) to the radio frequency reader(s)(14) over a local area network (59) or a wide area network (60)(for example an ethernet controller (86) as shown in the example of FIG. 3), thereby allowing the computer user (21) to reprogram the programmable module (26) to correspondingly alter the operation of the animal monitoring device (6) even when the bolus (4) containing the animal monitoring device (6) resides within or is attached to the animal (3).

Now referring primarily to FIG. 2, the specialized computer (18) configured to allow access by the computer user (21) to the sensed animal characteristic values (20) associated with an animal identification value (19) is described herein in terms of functional block components, screen shots, and various process steps. It should be appreciated that such functional blocks may be realized by any number of hardware or software components configured to perform the specified functions. For example, the animal monitoring system may employ various integrated circuit components which function without limitation as: memory elements, radio frequency signal modulators, processing elements, logic elements, look-up tables, or the like, which may carry out a variety of functions under the control of one or more microprocessors or other control devices.

Similarly, the software elements of the present invention may be implemented with any programming or scripting language such as C, C++, Java, COBOL, assembler, PERL, Labview or any graphical user interface programming language, extensible markup language (XML), Microsoft's Visual Studio .NET, Visual Basic, or the like, with the various algorithms or Boolean Logic being implemented with any combination of data structures, objects, processes, routines or other programming elements. Further, it should be noted that the present invention might employ any number of conventional wired or wireless techniques for data transmission, signaling, data processing, network control, and the like.

It should be appreciated that the particular computer implementations shown and described herein are illustrative of the invention and its best mode and are not intended to otherwise limit the scope of the present invention in any way. Indeed, for the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical animal monitoring system (1).

As will be appreciated by one of ordinary skill in the art, the present invention may be embodied in the alternative as a method, a data processing system, a device for data processing, a computer program product, or the like. Accordingly, the present invention may take the form of an entirely software embodiment, an entirely hardware embodiment, or an embodiment combining aspects of both software and hardware. Furthermore, the present invention may take the form of a computer program product on a computer-readable storage medium having computer-readable program code means embodied in the storage medium. Any suitable computer-readable storage medium may be utilized, including hard disks, CD-ROM, optical storage devices, magnetic storage devices, ROM, flash RAM, or the like.

It will be understood that each functional block of the block diagrams and the flowchart illustrations, and combinations of functional blocks in the block diagrams and flowchart illustrations, respectively, can be implemented by computer program instructions. These computer program instructions may be loaded onto a general purpose computer, special purpose computer or other programmable data processing apparatus to produce a machine, such that the instructions which execute on the computer or other programmable data processing apparatus for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of elements for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware based computer systems which perform the specified functions or steps, or suitable combinations of special purpose hardware and computer instructions.

Again referring to FIG. 2, the computer implemented animal monitoring system (1) can include a specialized computer (18) for receiving, processing and transforming a first radio frequency signal (13) from a reception device (17) to generate animal identification values (19) and sensed animal characteristic values (20) accessible by the computer user (21)). The specialized computer (18) can include at least one processing unit (27), a memory element (28), and a bus (29) which operably couples components of the computer (18), including, without limitation the memory element (28) to the processing unit (27). The computer (18) may be a conventional computer, a distributed computer, or any other type of computer which may contain all or a part of the elements described or shown to accomplish the functions described herein; the invention is not so limited. The processing unit (27) can comprise without limitation one central-processing unit (CPU), or a plurality of processing units which operate in parallel to process digital information, or a digital signal processor (DSP) plus a host processor, or the like. The bus (29) can be without limitation any of several types of bus configurations such as a memory bus or memory controller, a peripheral bus, and a local bus using any of a variety of bus architectures. The memory element (28) can without limitation be a read only memory (ROM)(30) or a random access memory (RAM)(31), or both. A basic input/output system (BIOS)(32) containing routines that assist transfer of data between the components of the specialized computer (18), for example during start-up, can be stored in ROM (30). The computer (18) can further include a hard disk drive (33) for reading from and writing to a hard disk (not shown), a magnetic disk drive (34) for reading from or writing to a removable magnetic disk (35), and an optical disk drive (36) for reading from or writing to a removable optical disk (37) such as a CD ROM or other optical media.

The hard disk drive (33), magnetic disk drive (34), and optical disk drive (36) and the reception device (17) can be connected to the bus (29) by a hard disk drive interface (38), a magnetic disk drive interface (39), and an optical disk drive interface (40), and a reception device interface (41), respectively. The drives and their associated computer-readable media provide nonvolatile storage of computer-readable instructions, data structures, program modules and other data for the computer (18). It can be appreciated by those skilled in the art that any type of computer-readable media that can store data that is accessible by a computer, such as magnetic cassettes, flash memory cards, digital video disks, Bernoulli cartridges, random access memories (RAMs), read only memories (ROMs), RFID devices or the like, may be used in the exemplary operating environment.

The computer (18) can further include an operating system (42) and an animal monitoring program (43)(AMP) which as to particular embodiments of the invention can include an animal monitoring device encoder-decoder module (44)(AMD encoder-decoder module) for programming animal identification values (19) to the animal monitoring device (AMD)(6).

Which as to particular embodiments can be accomplished using an animal monitoring device programmer (45) connected to the bus (29) by an AMD interface (46). The AMD encoder-decoder module (44) can be stored on or in the hard disk, magnetic disk (35), optical disk (36), ROM (30), in RAM (31) of the specialized computer 8) or alternately the functionalities of the AMD encoder-decoder module (44) may be implemented as an application specific integrated chip (ASIC) or file programmable gate array (FPGA), or the like.

As to particular embodiments, the specialized computer (18) can be further configured to generate programming data (24A) based on computer user (21) interaction (whether a part of or discrete from the AMD interface (46)), which can be received over the LAN (59) or the WAN (60) by the RF reader (14). The RF reader (14) can generate a second radiofrequency signal (24) to carry the programming data (24A) which can be received by the radio frequency signal receiver (23) contained in the animal monitoring device (6). The second radio frequency signal (24) can be processed by the microcontroller (7) to reprogram the programmable module (26) to correspondingly alter the operation of the animal monitoring device (6), regardless as to whether the bolus (4) containing the animal monitoring device (6) has a location outside of the animal (3) or has a location inside of the animal (3).

The computer user (21) can enter commands and information into the computer (18) through input devices such as a keyboard (47) and a pointing device (48) such as a mouse. Other input devices (not shown) may include a microphone, joystick, game pad, satellite dish, scanner, magnetic strip of a card, or the like. These and other input devices are often connected to the processing unit (27) through a serial port interface (49) that can be coupled to the bus (29), but may be connected by other interfaces, such as a parallel port, game port, or a universal serial bus (USB). A monitor (50) or other type of display device can also be connected to the bus (29) via interfaces such as a video adapter (51), or the like. In addition to the monitor (50), the computer (18) can further include a peripheral output device (52), such as speakers and printers.

A "click event" occurs when the computer user (21) operates at least one function of the AMP (43) or the animal monitoring device encoder-decoder module (44), or other program or other application function, through an action or the use of a command which for example can include pressing or releasing a left mouse button (53) while a pointer element (54) is located over a control icon (55) displayed on the monitor (50). However, it is not intended that a "click event" be limited to the press and release of the left mouse button (53) while a pointer element (54) is located over a control icon (55). Rather, the term "click event" is intend to broadly encompass any action or command by the computer user (21) through which a function of the operating system (42) or animal monitoring program (43), animal monitoring device encoder-decoder module (44), or other program or application is activated or performed, whether through clickable selection of one or a plurality of control icon(s) (55) or by computer user (21) voice command, keyboard stroke(s), mouse button, touch screen, touch pad, or otherwise. It is further intended that control icons (55) can be configured without limitation as a point, a circle, a triangle, a square (or other geometric configurations or combinations or permutations thereof), or as a check box, a drop down list, a menu, or other index containing a plurality of selectable options, an information field which can contain or which allows input of a string of alphanumeric characters such as a street address, zip code, county code, or natural area code, animal identification number or by inputting a latitude/longitude or projected coordinate X and Y, animal pen number, or other notation, script, character, or the like.

The computer (18) may operate in a networked environment using logical connections (56) to one or a plurality of remote second computers (22). These logical connections (56) can be achieved by a communication device (58) coupled to or a part of the computer (18). Each of the plurality of remote second computers (22) can include a part or all of the elements as included in the specialized computer (18) although only a single box has been illustrated in FIG. 2 for the remote second computer (22). The logical connections (56) depicted in FIG. 2 can establish a local-area network (LAN)(59) or a wide-area network (WAN)(60). Such networking environments are commonplace in offices, enterprise-wide computer networks, intranets and the Internet (61).

When used in a LAN (59) networking environment, the computer (18) can be connected to the local network through a network interface (62). When used in a WAN (60)-networking environment, the computer (18) typically includes a modem (63), or other type of communications device, for establishing communications over the WAN (60), such as the Internet (61). The modem (63), which may be internal or external to the specialized computer (18), can be connected to the bus (29) via the serial port interface (49). In a networked environment, the animal monitoring program (43), or portions thereof, may be stored in any one or more of the plurality of remote second computers (22). It is appreciated that the logical connections (56) shown are exemplary and other hardware elements and communications elements can be utilized for establishing a communications link between the specialized computer (18) and one or more of the a plurality of remote second computers (22).

While the computer elements and the network elements shown in FIG. 2 can be utilized to practice the invention including the best mode, it is not intended that the description of the best mode of the invention or any preferred embodiment of the invention be limiting with respect to the utilization of a wide variety of similar, different, or equivalent computer elements or network elements to practice embodiments of the invention which include without limitation hand-held devices, such as personal digital assistants or camera/cell phone, multiprocessor systems, microprocessor-based or programmable consumer electronics, network PCs, minicomputers, mainframe computers, PLCs, or the like.

Now referring primarily to FIGS. 1 and 3, the RF reader (14) can receive the first radio frequency signal (13) from the AMD (6) inside the bolus (4) implanted in, retained by, attached to, or held in the reticulum (5) of an animal (3). The AMD (6) within the bolus (4) can send encoded animal identification information (12) and the encoded sensed animal characteristic information (11) using the first radiofrequency signal (13), as above described.

One illustrative embodiment of the RF reader (14) as shown in FIGS. 1 and 3, provides a reader microcontroller (64) which includes a reader processor (65) which controls the functions of a variety of reader processor elements (66) stored in a reader memory element (67) each of which provides a response to events related to receiving the first radiofrequency signal (13) from the AMD (6) within the bolus (4) carrying encoded animal identification information (12) and sensed animal characteristic information (11), or receiving reader sensor signals (68) from reader sensors (69) which monitor environmental parameters proximate the RF reader (14) such as ambient temperature (70); or generating data packets (16) which include all or parts of such information, or sending data packets (16) to the computer (18) or a remote second computer (57) for access by a computer user (21). A reader microcontroller (64) suitable for use with embodiments of the RF reader (14) can be obtained from Microchip Technology. Inc., 2355 West Chandler Blvd., Chandler, Ariz., Part No. PIC18F4620-I/PT, or similar or equivalent components can be suitable as a reader microcontroller (64) programmable to perform the above-described functions of the RF reader (14).

Again referring primarily to FIG. 3, a reader antenna (71) can receive encoded animal identification information (12) and encoded sensed animal characteristic information (11) and other information generated by operation of the AMD (6) within the bolus (4) attached to, implanted in, or retained in an animal (3). The reader antenna (71) can be tuned to the first radiofrequency signal (13) generated by the AMD (6) by a reader matching network element (72). A reader receiver (73)(or transceiver) can be controlled by a first reader processor element (74) to convert the first radiofrequency signal (13) received by the reader antenna (71) from analog to digital baseband signals.

Again referring primarily to FIG. 3, the reader sensor (69) can take the form of an ambient temperature sensor (75) which can be located to sense the ambient temperature (70) surrounding the RF reader (14). The ambient temperature sensor (75) can take the form of a thermistor. A suitable thermistor for use in embodiments of the RF reader (13) is available from Microchip Technology, Inc., 2355 West Chandler Blvd., Chandler, Ariz., Part No. MCP98242, and similar and equivalent parts. The ambient temperature sensor (75) can be operated under the control a second reader processor (76) which functions to regulate power to the ambient temperature sensor (75) and converts the reader sensor signal (68) from the ambient temperature sensor (75) into a digital representation of the ambient temperature (70). The second reader processor (76) can further function to encode or re-encode from time to time an amount of reader temperature calibration data (77) which allows calculation and output of an ambient temperature value (78).

Again referring primarily to FIG. 3, a clock element (79) can operate under the control of a third reader processor element (80) to generate a date and time signal (81) that represents a date and time value (82).

Again referring primarily to FIG. 3, a fourth reader processor element (83) can function to assemble data packets (16) which as an example can include a representation of, the ambient temperature value (78) and the date and time value (82) at which the information from the AMD (6) was received by the RF reader (14). The assembled data packet (16) can be stored and retrieved from the reader memory element (67) under the control of the fourth reader processor element (83).

Again referring primarily to FIG. 3, a fifth reader processor element (84) can function to provide an ether net interface (85) for an ether net controller (86) to receive instructions or requests from the computer (18)(or remote computer (57). The fifth reader processor (84) can further function as a second radio frequency generator (25) and transmit the second radio frequency signal (24) to reprogram the programmable module (26) of the animal monitoring device (6) within the bolus (4). The fifth reader processor element (84) can further function to send the retrieved data packets (16) to the ether net controller (86) for transmission to the computer (18).

Now referring primarily to FIGS. 4 through 6, embodiments of the animal monitoring system (1) can include an inert bolus (4) orally administrable to an animal (or implantable in an animal) (3) containing the AMD (6) which includes one or more of a microcontroller (7), one or more processors (8), at least one sensor (9), and a first radio frequency generator (87) including one or more of an oscillator (88), a radio frequency stabilizer (89), an antenna (90), and a power source (91) which operate to generate the first radio frequency signal (13). As to particular embodiments the AMD (6) can further include a radio frequency signal receiver (23) which functions to receive a second radio frequency signal (24) including instructions input by a user (21) by interaction with specialized computer (18) to reprogram the programmable module (26) of the microcontroller (7). Additionally, a first magnet (92)(as shown in the example of FIG. 5) or a pair of magnets (93)(as shown in the example of FIG. 4) can be further included in the bolus (4).

Embodiments of the bolus (4) which are orally administered to an animal (3) can provide an inert bolus body (94) having external dimensional relations adapted to allow oral administration and retention of the bolus (4) in a part of the stomach, such as the reticulum (5) of a particular species of animal (3). As one non-limiting example, the inert bolus body (94) can include an amount of cured plastic resin (95) cast about the animal monitoring device (6) including those embodiments which further include the first magnet (92) or further include the pair of magnets (93). The amount of cured plastic resin (95) can for example comprise a plastic resin such as urethane resin, epoxy resin, polyester resin, or the like used in accordance with the manufacturer's instructions. As to other embodiments, the inert bolus body (94) can comprise a sealable container (96) which defines a hollow inside space (97) which receives the animal monitoring device (6) and can further receive the first magnet (92) or further receive the pair of magnets (93). As to other embodiments, the sealable container (96) having the animal monitoring device (6) received in the hollow space (89)(and as to particular embodiments further including the first magnet (92) or the pair of magnets (93) received in the hollow space) can have the amount of cured plastic resin (95) cast about the animal monitoring device (6), located within the sealable container (96) (and about the first magnet (92) or about the pair of magnets (93) depending upon the embodiment.

As one illustrative example, a bolus (4) suitable for oral administration to an animal (3) can be generally cylindrical with a diameter in the range of about one-half inch to about one inch and having a length disposed between a first bolus end (98) and a second bolus end (99) in the range of about two inches and about five inches. Particular embodiments of the bolus (4) can have a length of about three and one-half inches and a diameter of about three-quarters of an inch. While the Figures show the bolus (4) in the constructional form of a cylinder with discrete end caps (100)(101); the invention is not so limited, and the bolus (4) can have numerous and varied external surface configurations which allow oral administration and retention within the reticulum (5)(or other part of the digestive tract) of an animal (3). Typically, retention of the bolus (4) in a part of a stomach, or retention by way of implant, will be for all or a substantial portion of the life of the animal (3). The inert bolus body (94) can be molded, cast, machined, or otherwise fabricated from biocompatible (or biologically inert) non-magnetic materials which allow transmission of the first radio frequency signal (13) from within the bolus (4) to outside of the animal (3). As examples, the inert bolus body (94) can be made from plastics such as nylon, fluorocarbon, polypropylene, polycarbonate, urethane, epoxy, polyethylene, or the like; or metals such as stainless steel; or other materials such as glass can be utilized.

The hollow inside space (97) inside of the inert bolus body (94) can be of sufficient volume to house one or more of the microcontroller (7), the sensor (9), the radio frequency generator (87)(such as an oscillator (88), the radio frequency stabilizer (89), the antenna (90) and the power source (91) along with the associated circuitry. As to particular embodiments, the hollow inside space (97) can have sufficient volume to further house a first magnet (92)(as shown in the example of FIG. 5) and as to other embodiments of the inert bolus body (94), the hollow inside space (97) can have sufficient volume to further house non-conductive insulators (102), and non-conductive spacers (103) to establish a particular distance between a pair of magnets (93)(as shown in the example of FIG. 4).

As to embodiments of the bolus (4) as shown in FIGS. 4 and 5 or similar embodiments, the hollow inside space (97) can be configured as a cylindrical volume having a diameter of about three-eighths of an inch and about five-eighths inch and a length disposed between the first bolus end (98) and the second bolus end (99) of between about two inches and about four inches. A particular non-limiting embodiment of the hollow inside space (97) can be about one-half inch in diameter and having a length of about three inches.

As to those embodiments of the bolus (4) including a sealable container (96), the sealable container (96) can further provide at least one discrete end cap (100) removably sealable with a first bolus end (98) or a second bolus end (99) or both ends (98)(99) of the bolus (4) to allow access to the hollow inside space (97) for location of the various components of the animal monitoring device (6). As to certain embodiments, the bolus (4) can take the form of a closed end tube having one end cap (100) or a cylindrical tube having a discrete end cap (100)(101) fitted to each of the first bolus end (98) and the second bolus end (99). The end cap(s) (100)(101) can also take the form of a plug sealably inserted into one or both ends of the sealable container (96), as shown in FIGS. 4 and 5. Alternately, the end cap(s) (100)(101) and the bolus (4) can provide rotatably matable spiral threads. Additionally, the end cap(s) (100)(101) can take the form of a permanent seal to one or both ends of the sealable container (96) of the bolus (4) such as a castable polymer which cures to seal the first bolus end (98) or the second bolus end (99) or both ends of the bolus (4). The bolus (4) can also take the form of matable halves (whether longitudinal or latitudinal) which can avoid the use of end caps (100)(101).

The bolus (4) having a hollow inside space (97) can be generated by a wide variety of procedures such as molding, casting, fabrication or the like. As one non-limiting example, a cylindrical tube having an external diameter and an internal diameter, as above described, can be divided into sections of suitable length to which the end caps can be fitted. Alternately, a bore can be made in a cylindrical solid rod having an external diameter, as above described, to provide a closed end tube with the bore having sufficient dimension to provide the hollow inside space (97). An end cap (100)) or seal can be fitted to the open end of the closed end tube.

Now referring primarily to FIGS. 4 through 6, a printed circuit board (104) can be utilized to mechanically support and electrically connect the microcontroller (7), the sensor (9), the first radio frequency generator (87)(such as an oscillator (88)), the radio frequency stabilizer (89), and the antenna (90). The printed circuit board (104) can be configured as a disk having a circular boundary (105) and a thickness disposed between two generally planar surfaces (106)(107). The disk shaped printed circuit board (104) can be disposed with the planar surfaces (106)(107) in substantially perpendicular relation to a longitudinal axis (108) of the hollow inside space (97) when configured as a cylindrical volume, as shown in FIG. 4 or 5; however, the invention is not so limited, and the components can be mounted on any suitable supporting surface in any configuration or arrangement which allows the components to function as further described below.

Again referring primarily to FIG. 6, a block diagram represents the various integrated circuit components of the animal monitoring device (6) which function as processing elements, memory elements, logic elements, look-up tables, or the like, to carry out a variety of functions under the control of one or more microprocessors or other control devices, as further described below. As to the embodiments shown in FIGS. 4 through 6, the microcontroller (7) can take the form of a small computer on one or more integrated circuits having one or more processors (8) which control one or more processing elements (109) stored in a programmable memory module (26) each of which provides a response to events related to the surveillance, identification, and measurement of values in relation to an individual animal (3). A microcontroller (7) available from Microchip Technology. Inc., 2355 West Chandler Blvd., Chandler, Ariz., Part Nos. PIC18LF14K22 or PIC18LF15K22, or similar or equivalent components, can be suitable for use with embodiments of the animal monitoring device (6).

A first processor element (111) can function to encode and continuously or intermittently output an amount of encoded animal identification information (12) which can represent an animal identification value (19) such as bolus identification number (112), an animal identification number (113), or other value which associates information received from a bolus (4) to one particular animal (3) or object. the animal bolus identification number (112), the animal identification number (113), or other value which associates information received from a bolus (4) with a particular animal can be recoded by operation of the fifth processor element (144) as further described below.

A second processor element (114) can function to intermittently output an amount of encoded sensed animal characteristic information (11) representing a sensed animal characteristic (2) of an animal (3) or object. For the purposes of this invention, an sensed animal characteristic (2) of an animal (3) or object can include any one or more of a physiological characteristics of the animal (3) such as temperature, pH, conductivity of a fluid, heart rate, blood pressure, partial pressures of dissolved gases, or the like; or a non-physiological parameter such as animal location, animal tilt, humidity, or the like. The second processor element (114) can in part function to receive analog signals or digital signals ("sensor signals" (10)) from one or more sensor(s) (9) configured to sense a particular animal characteristic (2). As a non-limiting examples, the sensor (9)(or sensors) can be an omnidirectional tilt and vibration sensor (PN SQ-SEN-200) distributed by Signal Quest Precision Microsensors; a betachip thermistor (PN 1K2OG3) distributed by BetaTHERM Sensors; a humidity sensor (PN HCZ-D5) distributed by Ghitron Technology CO., Ltd; an ultra miniature pressure transducer (PN COQ-062) distributed by Kulite, a proximity sensor (PN PY3-AN-3) distributed by Automation Direct.com, a conductivity sensor as distributed by Hach Company, (PN D3725E2T). The second processor element (114) can be reprogrammed to adjust the amount of data collected from each sensor (9), rate of data collection, and the elapsed time between collection periods. Additionally, the second processor element can be recoded to activate or deactivate one or more of the sensors (9).

Variation of the sensed animal characteristic(s)(2) can be continuously or intermittently updated by encoding or recoding the a digital representation of the signal generated by the sensor (9). The second processor element (114) can further function to encode or recode from time to time an amount of sensor calibration data (115) which allows calculation and output of a sensed animal characteristic value (20) of the animal (3). As to the particular embodiment of the invention shown in FIGS. 4 and 5, the second processor element (114) can receive and encode signals received from a thermistor (57) (a type of resistor whose resistance varies with change in temperature). A suitable thermistor for use in embodiment of the invention is available from Microchip Technology, Inc., 2355 West Chandler Blvd., Chandler, Ariz., Part No. MCP98242, and similar and equivalent parts.

A third processor element (116) functions to control the first radio frequency generator (87)(for example, oscillator (88) to generate a stable first radio frequency signal (13). An oscillator (88) suitable for use with the invention is available from Freescale Semiconductor, Part No. MC1319x, MC1320x, MC1321x, and MC1322x, and similar or equivalent parts. The third processor element (116) can further function to control a radio frequency stabilizer (89) which functions to offset oscillator (88) wave flux caused by changes in temperature or power to the oscillator (88). A frequency stabilizer (89) suitable for use with the invention is available from Hope Microelectronics Co., Ltd, Part No. HF433E, RF Monolithics, Inc., Part No. RF1172C, and similar or equivalent parts. In regard to the particular embodiment of the invention shown in FIGS. 4 and 5, the oscillator (88) and frequency stabilizer (89) can generate a first radio frequency signal (13) stable between about 410 MHz and about 440 MHz, about 800 MHz or about 900 MHz. A particular embodiment of the invention generates a first radio frequency signal (13) of about 433 MHz.

The third processor element (116) can be recoded by operation of the fifth processor element (144) to change the frequency of the first radio frequency (13) as selected by a user (21) by interaction with the specialized computer (18). For example from 433 MHz to 900 MHz, or to scan the available frequencies, or intermittently switch frequencies. The RF reader (14) can be correspondingly configured to receive the first radio frequency signal (13) at any one or a combination of these radio frequencies whether intermittently, continuously, or alternating between these radio frequencies as selected by the user (21).

A fourth processor element (117) functions to control a network frequency match element (118). The network frequency match element (118) can include capacitors and resistors in combination to deliver a particular first radio frequency signal (213) under the conditions of the method utilized (for example the method above described) to the antenna (90). As a non-limiting example, the network frequency match element (118) can detune a 433 MHz first radio frequency signal (13) to generate a signal of between about 418 MHz and about 425 MHz. The detuned signal can compensate for demodulation of the radio frequency signal (13) due to interaction with the mass of animal (3). The degree of demodulation can be substantially consistent and repeatable from animal (3) to animal (3). Accordingly, the network frequency match element (118) can be configured to compensate for the signal demodulation due to the unique mass of an animal (3) such that the first radio frequency signal (13) transmitted outside of that unique mass of the animal (3) can be at about 433 MHz (or other selected frequency).

A fifth processor element (117) functions to decode the second radio frequency signal (24) and based on user (21) interaction with the specialized computer (18) reprogram or alter the function of the one or more processing elements (109) as above described.

As to particular embodiments, the antenna (90) can be imprinted on the printed circuit board (104) proximate the circular boundary (105) to provide an antenna (90) of generally partial circular configuration having a length of about 37 millimeters and a width of about 1 millimeter (as shown in the examples of FIGS. 4 and 5). The antenna (90) operates to transmit the first radio frequency signal (13) at the wavelengths above described. An advantage of this configuration of antenna (90) can be that it does not require winding upon or interaction with the magnetic field (119) of the first magnet (92) or one or both of a pair of magnets (93)(or any magnet) to transmit a first radio frequency signal (13). Accordingly, this configuration of antenna (90) can provide a lesser amount of interference from the magnetic field (119) of the first magnet (92) or the pair of magnets (93) contained in the bolus (4) resulting a lower incidence of loss of the first radio frequency signal (13), less modulation of the first radio frequency signal (13) which results in a greater consistency (or lesser amount of lost data) in transmission of animal identification information (12) and sensed animal characteristic information (11).

Again referring to FIGS. 4 and 5, the bolus (4) can further include a power source (91) located within the hollow inside space (97). The power source (91) as shown in FIGS. 4 and 5 can take the form of a battery (120) such as a AA battery, a AAA battery, or the like. The battery (120) can be inserted or stacked within the hollow inside space (97) proximate the printed circuit board (104). A non-conductive insulator (102) can be disposed between the printed circuit board (104) and the power source (91). The power source (91) provides power to the electronic components supported on the printed circuit board (104). A first battery lead (121) connects the positive battery terminal (122) of the printed circuit board (104) to the positive pole (123) of the battery (120) (or power source) and a second battery lead (124) connects the negative battery terminal (125) of the printed circuit board (104) to the negative pole (126) of the battery (120)(or power source).

Now referring primarily to FIG. 4, in particular embodiments of the invention a first non-conductive spacer (127) can be disposed in the hollow inside space (97) of the bolus (4) adjacent to the printed circuit board (104) and a second non-conductive spacer (128) can be disposed in the hollow inside space (97) of the bolus (4) adjacent the battery (120). A first of the pair of magnets (129) can be disposed adjacent the first non-conductive spacer (127) and a second of the pair of magnets (130) can be disposed adjacent the second non-conductive spacer (128). The first of the pair of magnets (129) and the second of the pair of magnets (130) can be configured as magnetic disks or cylinders each having a pair of opposed circular faces disposed a distance apart by the thickness of the magnet (129)(130). By providing a pair of magnets (93) disposed a distance apart, a first magnetic field (131) generated by the first of the pair of magnets (129) and a second magnetic field (132) generated by the second of the pair of magnets (130) can attractingly interact with metal objects (133), such as coins, washers, wire, nails, tacks, barbs from barbed wire, or the like, ingested by the animal (3) to magnetically engage these metal objects (133) with the external surface of the bolus (4). Typically, the axis of greatest length of the metal objects (133) will generally align with the longitudinal axis (108) of the bolus (4) reducing the distance that the metal object (133) extends outwardly from the external surface of the bolus (4) Depending upon the configuration of the external surface of the bolus (4), the size, power, and distance separating the first of the pair of magnets (129) and the second of the pair of magnet (130) can be adjusted to correspondingly adjust the interaction of the first magnetic field (131) and the second magnetic field (132) to act on metal objects (133), as above described. For example, in the embodiment of the invention shown in FIG. 4, either the particular configuration of the first of the pair of magnets (129) and the second of a pair of magnets (130) (dimensional relations and power) or the particular configuration of the first non-conductive spacer (127) and the second non-conductive spacer (128) can be adjusted to correspondingly alter the interaction of metal objects (133) with the external surface of the bolus (4). A second advantage of providing a pair of magnets (93) disposed a distance apart, can be that the printed circuit board (104) can be located between, and a sufficient distance from, either of the pair of magnets (93) to reduce interference with the transmission of the radio frequency signal (13).

Again referring primarily to FIG. 4, the printed circuit board (104) supporting the electronic components, the non-conductive insulator (102), the non-conductive spacers (127)(128), and the pair of magnets (93) can be overwrapped with a non-conductive wrap element (134) to allow the several elements to moved as a single piece. As one non-limiting example, the non-conductive wrap element (134) can comprise a plastic tube shrinkable in dimension by application of heat to conform the external surface of the components aligned as above described. Accordingly, the overwrapped elements can be inserted into the hollow inside space (97) as a single piece and the at least one end cap (100) can be sealably engaged with first bolus end (98) or second bolus end (99) of the bolus (4). The non-conductive wrap element (134) can have one or more apertures (135). An amount of cured plastic resin (95), as above described, prior to curing can flow through the one more apertures (135) to be cast about the components of the animal monitoring device (6).

Now referring primarily to FIG. 5, other embodiments of the invention can have a constructional as above described and shown in FIG. 4 with the exception of the form and placement of the pair of magnets (93). In the embodiment shown in FIG. 5, the pair of magnets (93) and their corresponding magnetic fields (131)(132) along with the non-conductive spacers (127)(128) can be replaced by a first magnet (92) placed adjacent the animal monitoring device (6) and as to those embodiments having a non-conductive wrap element (134) located outside of the non-conductive wrap (134). The animal monitoring device (6) along with the first magnet (92) can be located inside of the inert bolus body (94) whether within an amount of cured plastic resin (95) or within a sealable container (96)(whether or not the sealable container (96) is also filled with an amount of cured plastic resin (95). As to particular embodiments, the first magnet (92) can have a first and second opposed magnetic faces (136)(137) defining a south pole (138) and a north pole (139), with the first magnetic face (136)(as to the embodiment shown the south pole (138)) disposed in inward facing relation to the animal monitoring device (6) and the second magnetic face (137)(as to the embodiment shown the north pole (139)) disposed in outward facing relation to said animal monitoring device (6). As to certain preferred embodiments, the first magnet (92) can have a generally rectangular shape having four sides (140) defining the area of a first magnet face (136)(south pole (138)) and the second magnet face (137)(north pole (139)) disposed in substantially parallel opposed relation a distance apart with the first magnet face (136)(south pole (138)) disposed in inward facing relation to the animal monitoring device (6).

Figure 7:
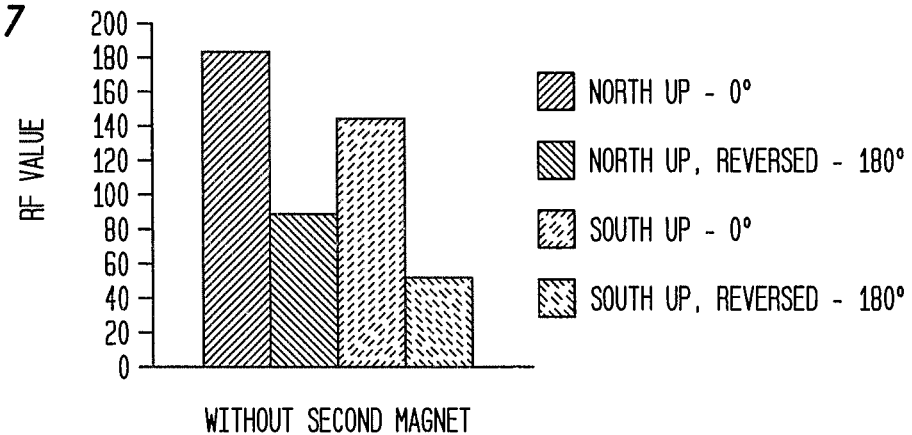
FIG. 7 is a bar graph which compares strength of radio frequency transmission against orientation of magnetic field of a first magnet contained in bolus.

Now referring primary to FIG. 7, a bar graph plots the strength of the first radio frequency (13) against the orientation of the first magnet (92) in relation to the animal monitoring device (6) located within the inert bolus body (94)(as described for embodiments similar to that shown in FIG. 5). Importantly, the orientation of the first magnet (92) in relation to the animal monitoring device (6) can result in a substantial difference in the strength of the received first radio frequency signal (13) outside of the bolus (4). Placement of the first magnet (92) with the second magnetic face (137)(north pole (139)) facing outward in relation to the animal monitoring device (6) (north pole designated as "north up" in FIG. 7) increases the strength of the received first radio frequency signal (13) from the animal monitoring device (6) outside of the bolus (4) as compared to having the first magnetic face (136)(south pole (138)) facing outward in relation to the animal monitoring device (6)(south pole designated as "south up" in FIG. 7). Depending upon the type and kind of the first magnet (92), the method in accordance with embodiments of the invention, defines the first magnetic face (136) as the magnetic face which in inward facing relation to the animal monitoring device (6) increases strength of the first radio frequency signal (13) received at the radio frequency reader (14). The first magnetic face (136) may define the south pole (138) as described; however, the invention is not so limited, and the first magnetic face (136) may also define the north pole (139) of the first magnet (92), the method selecting the first magnetic face (136) as that face which in the inward facing relation to the animal monitoring device (6) produces the greater strength of first radio signal frequency (13) outside of the bolus (4).

Additionally, having placed the first magnetic face (136) (south pole (138)) facing inwardly to increase strength of the received first radio frequency signal (13), the first magnet (92) can be rotated to through 180 degrees to find the orientation which further increases the strength of the first radio frequency signal (13) outside of the bolus (4). As shown by FIG. 7, the first magnetic (92) having the first magnetic face (135)(south pole (138)) facing inwardly in relation to the animal monitoring device (6) and the elongate body of the first magnet (92) substantially aligned with the longitudinal axis (108) of the animal monitoring device (6) is oriented at zero degrees of rotation in relation to the longitudinal axis (108) (as shown in the example of FIG. 5). As to this embodiment of the invention, this orientation can produce a substantially increased strength of received first radio signal frequency (13) outside of the bolus (4) as compared to having the opposed magnet ends (141)(142) oriented at 180 degrees of rotation in relation to the longitudinal axis (100)(not shown).

Figure 8:
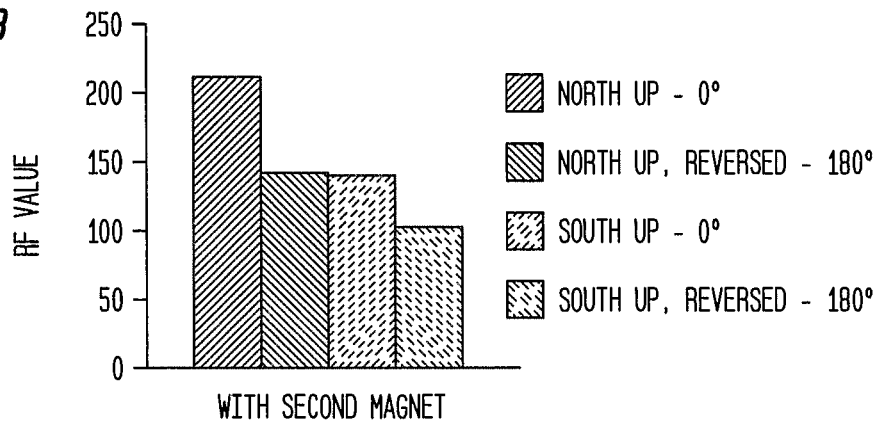
FIG. 8 is a bar graph which compares strength of radio frequency transmission against orientation of magnetic field of a first magnet contained in the bolus when magnetically coupled to a second magnet outside of the bolus.

Now referring primarily to FIGS. 5 and 8, embodiments of the invention can further include a second magnet (143) having a location outside of the bolus (4). The second magnet (143) can be orally administered to an animal (3) in similar fashion to the bolus (4). The second magnet (143) can comprise a conventional magnet orally administered to animals (3) to magnetically capture metal objects (133) within the rumen of the animal (3). Particular embodiments of the second magnet (143) can have dimensional relations the same or similar to the first magnet (92) located inside the inert bolus body (94). Interestingly, as shown in FIG. 8, magnetic coupling of the second magnet (143) to the first magnet (92) within the bolus (4) can increase the strength of the first radio frequency signal (13) outside of the bolus (4), regardless of orientation of the first magnet (92) within the bolus (4), even though the first magnet face (136)(south pole (138)) inwardly facing and in zero degree relation to the longitudinal axis (108) of the animal monitoring device (6) already had the greatest strength of the first radio frequency signal (13) outside of the bolus (4)(shown as "north up" in FIG. 7).

The results set out in the example shown by FIGS. 7 and 8, were achieved by submerging the bolus (4) of the embodiment shown in FIG. 5, and as above described, in an amount of saline solution prepared by dissolving about 27 grams of sodium chloride per liter of water. The bolus (4) submerged in the saline solution was placed about 25 feet from the RF reader (14) to approximate receiving a signal from a bolus (4) within the rumen of a ruminant animal (3) at 75 feet. The bolus (4) between trials was unaltered, except for the orientation of the first magnet (92) in relation to the animal monitoring device (6) contained inside the inert bolus body (86). The first magnet (92) was disposed in a first trial with the north pole (139) facing outwardly from the animal monitoring device, and in a second trial with the south pole (138) facing outwardly from the animal monitoring device (6). The designation of the first magnetic face (136) of the first magnet (92) was defined by the magnetic face which facing inwardly generates the greatest first radio frequency signal (13) received by the RF reader (14). Accordingly, as to the particular embodiment of the invention shown in FIG. 5, the south face (138) of the first magnetic (92) faces inwardly toward the animal monitoring device (6) and defines the first magnetic face (136), while the north pole (139) of the first magnet (92) faces outwardly in relation to the animal monitoring device (6) and defines the second magnetic face (137). The first face (136) being defined by the south pole (138) of the first magnet (92), a third trial was conducted in which the first magnet (92) was rotated 180 degrees in relation to the longitudinal axis (108) of the animal monitoring device (6) in reversed relation to the zero degree position. The strength of the first radio frequency signal (13) received by the RF reader (14) was determined and the first magnet (92) was placed in zero degree or 180 degree relation to the animal monitoring device (6). The results of the trials are set out in the bar graph shown in FIG. 7.

The results set out in the example shown by FIG. 8, were achieved by submerging the bolus (4) of the embodiment shown in FIG. 5 and above described in an amount of saline solution prepared by dissolving about 27 grams of sodium chloride per liter of water. The bolus (4) submerged in the saline solution was placed about 25 feet from the RF reader (14) to approximate receiving a signal from a bolus (4) within the rumen of a ruminant animal (3). As to each trial shown in FIG. 7, and described above, an additional trial was conducted by submerging a second magnet (143) in the saline solution in which the bolus (4) containing the first magnet (92) was submerged. In each trial, the second magnet (143) was allowed to magnetically couple the first magnet (92) and the strength of the first radio frequency signal (13) was determined. The results being summarized in the bar graph shown in FIG. 8. Interestingly, as shown by FIG. 9, magnetic coupling of the second magnet (143) with the first magnet (92) increased the strength of the first radio frequency signal (13).

The first radio frequency signal (13) strength calculated based on the reads gathered by the RF reader (14) during a period of 15 minutes and then multiplied by the signal to noise ratio to produce a RF value utilized to compare strength of radio frequency. As one illustrative example, for a particular bolus if the reads are 2 during the 15 minute period and the signal to noise ratio is 90.7 then the RF value is 181.4.

As can be easily understood from the foregoing, the basic concepts of the present invention may be embodied in a variety of ways. The invention involves numerous and varied embodiments of animal monitoring system including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an animal monitor" should be understood to encompass disclosure of the act of "monitoring an animal"—whether explicitly discussed or not—and, conversely, were there effectively disclosure of the act of "monitoring an animal", such a disclosure should be understood to encompass disclosure of "an animal monitor" and even a "means for animal monitoring." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "a memory element" refers to one or more memory elements. As such, the terms "a" or "an", "one or more" and "at least one" can be used interchangeably herein. Furthermore, a compound "selected from the group consisting of" refers to one or more of the elements in the list that follows, including combinations of two or more of the elements.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result.

Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the animal monitoring devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. An animal monitoring system, comprising:
   a) an inert bolus body adapted to allow oral administration to a ruminant animal;
   b) an animal monitoring device having a location inside said inert bolus body, including:
      i) at least one sensor which generates a signal which varies in relation to change in a sensed animal characteristic;
      ii) a sensor signal encoder which encodes said signal generated by said at least one sensor as encoded sensed animal characteristic information;
      iii) a radio frequency signal generator which includes an oscillator which generates a first radio frequency signal capable of carrying said encoded sensed animal characteristic information to a location outside of said ruminant animal;
      iv) an antenna which transmits said radio frequency signal and receives a second radio frequency signal; and
      v) a battery which supplies power to said animal monitoring device;
   c) a first magnet having a location inside said inert bolus body, wherein said first magnet has a pair of opposed faces defining a north pole and a south pole, said south pole disposed in inward facing relation to said animal monitoring device, said north pole disposed in outward facing relation to said animal monitoring device.

2. The animal monitoring system of claim 1, wherein said inert bolus body comprises a cured resin cast about said animal monitoring device.

3. The animal monitoring system of claim 1, wherein said inert bolus body comprises a sealable container which defines a hollow inside space which receives said animal monitoring device.

4. The animal monitoring system of claim 3, further comprising a cured resin cast about said animal monitoring device located within said sealable container.

5. The animal monitoring system of claim 1, wherein said first magnet has a generally rectangular shape having four sides defining the area of a first magnet face and a second magnet face disposed in substantially parallel opposed relation a distance apart, said first face disposed in inward facing relation to said animal monitoring device, said first face defining said south pole.

6. The animal monitoring system of claim 1, wherein said sensed animal characteristics is selected from the group consisting of: tilt, conductivity of a biological fluid, blood pressure, and partial pressures of dissolved gases.

7. The animal monitoring system of claim 1, further comprising an animal identification information encoder which encodes animal identification information associated with said sensed animal characteristic as encoded animal identification information.

8. The animal monitoring system of claim 7, further comprising a printed circuit board which supports and electrically connects each of said sensor signal encoder, said animal identification information encoder, said radio frequency signal generator, and said antenna.

9. The animal monitoring system of claim 8, wherein said printed circuit board has a circular boundary and said antenna comprises an imprinted antenna having only one generally circular configuration imprint disposed proximate said circular boundary of said printed circuit board.

10. The animal monitoring system of claim 1, wherein said battery comprises a dry cell battery.

11. The animal monitoring system of claim 1, further comprising a second magnet adapted to allow oral administration to a ruminant animal separate from said inert bolus body containing said animal monitoring device and said first magnet, wherein said second magnet magnetically coupled to said first magnet having said south pole disposed in inward facing relation to said animal monitoring device, said north pole disposed in outward facing relation to said animal monitoring device increases transmission of said first radio frequency signal capable of carrying said encoded sensed animal characteristic information.

12. The animal monitoring system of claim 1, further comprising one or more radio frequency readers which receive and send said encoded sensed animal characteristic information.

13. The animal monitoring system of claim 12, further comprising a reception device which receives said encoded sensed animal characteristic information sent by said one or more radio frequency readers.

14. The animal monitoring system of claim 13, further comprising a computer having a configuration to receive and provide a user access to said encoded sensed animal characteristic information.

* * * * *